United States Patent [19]

Kaneko

[11] 4,244,874

[45] Jan. 13, 1981

[54] 3,8-DIOXO-SCIRPEN-4β,15-DIOL ESTERS AND THEIR USE AS ANTITUMOR AGENTS

[75] Inventor: Takushi Kaneko, Fayetteville, N.Y.

[73] Assignee: Bristol-Myers Company, New York, N.Y.

[21] Appl. No.: 61,213

[22] Filed: Jul. 27, 1979

[51] Int. Cl.[3] .......... C07D 311/78

[52] U.S. Cl. .......... 260/345.2; 424/283

[58] Field of Search .......... 260/345.2

[56] References Cited

U.S. PATENT DOCUMENTS

| | | | |
|---|---|---|---|
| 3,428,652 | 2/1969 | Sigg et al. | 260/345.2 |
| 4,129,577 | 12/1978 | Ellison et al. | 260/345.2 |

FOREIGN PATENT DOCUMENTS

| | | | |
|---|---|---|---|
| 9134891 | 12/1974 | Japan | 260/345.2 |
| 9134892 | 12/1974 | Japan | 260/345.2 |

OTHER PUBLICATIONS

Murphy et al., Proc. Amer. Assoc. Cancer Res., 17, 90 (1976).
Haas et al., ibid., 18, 296 (1977).
Pathre et al., J. Agric. Food Chem., 24, 97 (1976).
Tatsuno et al., J. Pure and Applied Chem., 35, 309 (1973).
Grove, J. Chem. Soc. (C), 375 (1970).
Grove et al., Biochemical Pharmacology, 24, 959 (1972..
Wei et al., Biochem. and Biophys. Res. Comm., 57, 838 (1965).
Sigg et al., Helv. Chim. Acta, 48, 962 (1965).

*Primary Examiner*—Nicky Chan
*Attorney, Agent, or Firm*—David M. Morse

[57] ABSTRACT

A novel series of 3,8-dioxo-scirpen-4β,15-diol esters is provided for use as antitumor agents. Also provided are various novel intermediates used in the production of such compounds.

7 Claims, No Drawings

3,8-DIOXO-SCIRPEN-4β,15-DIOL ESTERS AND THEIR USE AS ANTITUMOR AGENTS

BACKGROUND OF THE INVENTION

1. Field of the Invention

The present invention relates to novel trichothecene derivatives, to processes for their production and to their use as antitumor agents for the inhibition of malignant tumors in mammals.

2. Description of the Prior Art

The trichothecene derivatives of the present invention all contain a 9,10 double bond and a 12,13-epoxy function. The basic skeleton and numbering system for this class of trichothecenes is shown below.

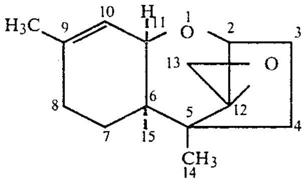

Various examples of both naturally occurring and semi-synthetic compounds of this class have been described in the literature. Illustrative of the more relevant publications are the following:

1. The compound anguidine (also called diacetoxyscirpenol) having the formula

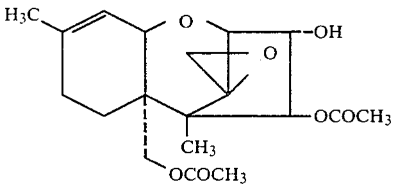

is disclosed as an antitumor agent in U.K. Pat. No. 1,063,255. Phase I clinical trials of anguidine in the United States have been reported in *Proc. Amer. Assoc. Cancer Res.* 17:90 (1976) and *Proc. Amer. Assoc. Cancer Res.* 18:296 (1977). Also disclosed (at least generically) are various derivatives of anguidine such as anguidol (also called scirpentriol or 3α,4β,15-trihydroxy-12,13-epoxytrichothec-9-ene), monodesacetylanguidine (presumably 15-acetoxy-3α,4β-dihydroxy-12,13-epoxytrichothec-9-ene or monoacetoxyscirpendiol) and esters of anguidine, anguidol and monodesacetylanguidine.

Monoacetoxyscirpenol and various esters of scirpentriol are also disclosed in *J. Agric. Food Chem.* 24(1): 97-103 (1976) as mycotoxins.

2. Japanese Published Applications Nos. J4 9,134,891 and J4 9,134,892 disclose T2 and HT2 toxins of the formula

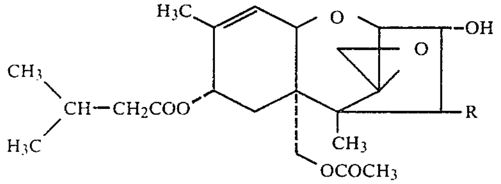

wherein R is —OH or

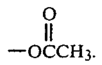

The compounds are said to be useful as antiviral agents.

3. U.S. Pat. No. 4,129,577 discloses anguidine derivatives of the formula

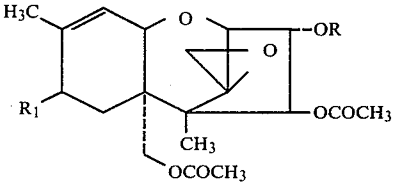

wherein $R_1$ is H or

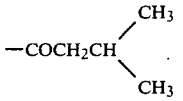

and R is an alkyl or aromatic group or is an acyl group

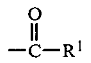

in which $R^1$ is an aliphatic, cycloaliphatic or aromatic group or a carbamate group —CONH—$R^1$. The compounds are useful as cytotoxic agents.

4. Neosolaniol having the formula

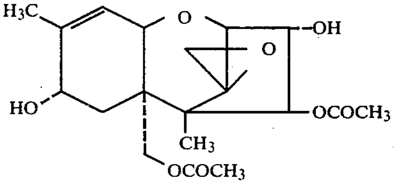

wherein the 8-hydroxy group is of the α-configuration is disclosed in *J. Pure and Applied Chemistry* 35(3):309 (1973) as a mycotoxin and inhibitor of protein synthesis.

5. U.S. Pat. No. 3,428,652 discloses anguidine derivatives of the formula

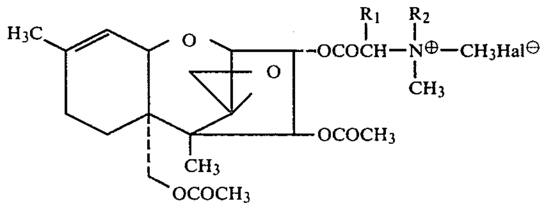

wherein $R_1$ is H and $R_2$ is methyl or, $R_1$ and $R_2$ together represent propylene, and Hal is Cl, Br or I. The compounds are reported to have antitumor activity.

6. Toxins isolated from culture filtrates of *F. scirpi* and having the formula

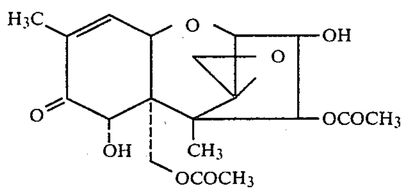

and

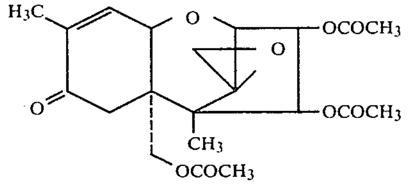

are disclosed in *J. Chem. Soc* (C), 375 (1970).

7. Trichothecene derivatives of the formula

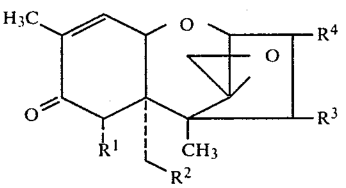

wherein $R^1$, $R^2$, $R^3$ and $R^4$ are —OH or —$OCOCH_3$ are disclosed in *Biochemical Pharmacology* 24:959-962 (1972) as having larvicidal activity. The degree of activity is said to be greatest in the compound where $R^1$=$R^2$=$R^3$=$R^4$=OH and least in the fully acetylated compound. It is suggested in the publication that the order of cytotoxic activity in this series is the same as the order of larvicidal activity.

8. The 12,13-epoxytrichothecenes of the general formula

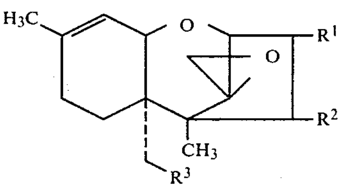

wherein $R^1$ and $R^3$ are H, OH or esterified OH and $R^2$ is OH, =O or esterified OH are described in *Biochemical and Biophysical Research Communications* 57(3): 838-844 (1974) as inhibitors of protein synthesis. The publication indicates that substitution of a carbonyl group at the C-8 position of the above compounds results in a moderate loss of activity and that substitution of a carbonyl group at $R^2$ results in complete loss of activity.

9. *Helvetica Chimica Acta* 48:962-988 (1965) discloses scirpentriol, various acetoxy esters of scirpentriol and the compound of the formula

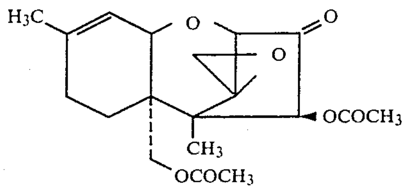

No biological properties of the 3-keto compound are indicated.

SUMMARY OF THE INVENTION

The present invention provides novel trichothecene derivatives of the general formula

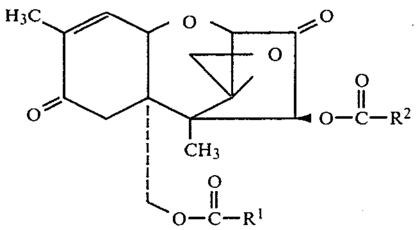

I wherein $R^1$ and $R^2$ are each independently (lower)alkyl; halo(lower)alkyl; alkenyl of the formula $—CR^3=C^4R^5$ in which $R^3$ is hydrogen, (lower)alkyl or 1'-halo(lower)alkyl and $R^4$ and $R^5$ are each independently hydrogen or (lower)alkyl; alkynyl of the formula $—C≡CR^6$ in which $R^6$ is hydrogen or (lower)alkyl; or a radical of the formula $$Ar—(CH_2)_m—$$

in which m is 0 or an integer from one to four and Ar is

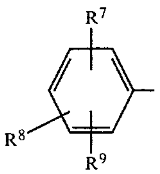

or

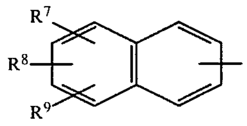

wherein $R^7$, $R^8$ and $R^9$ are each independently hydrogen, halogen, (lower)alkyl or (lower)alkoxy.

In another aspect the present invention provides compounds of the general formula

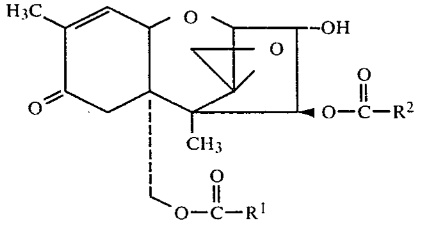

II and

-continued

III

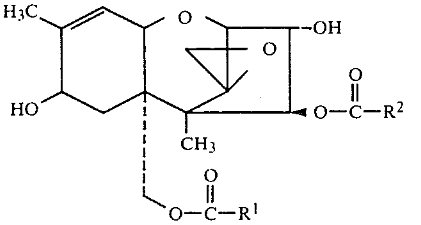

wherein $R^1$ and $R^2$ are as disclosed for the compounds of formula I, with the provisos that (1) $R^1$ and $R^2$ in formula II may not both be methyl and (2) when $R^1$ and $R^2$ in formula III is methyl, the 8-hydroxy group must be in the β-configuration.

The compounds of formulae I–III are antitumor agents for treatment of malignant tumors in mammals. Compounds of formulae II and III are also intermediates useful in the preparation of the compounds of formula I.

DETAILED DESCRIPTION

The various substituent groups disclosed above in connection with the novel compounds of the present invention may be further defined as follows:

(a) Halo or halogen includes chlorine, bromine, fluorine and iodine;

(b) (Lower)alkyl includes both straight and branched chain saturated aliphatic hydrocarbon radicals having from 1 to 4 carbon atoms inclusive, e.g. methyl, ethyl, n-propyl, isopropyl or n-butyl;

(c) (Lower)alkoxy includes $C_1$–$C_4$ alkoxy radicals, the alkyl portion of such radicals being defined as in (b) above. Examples include methoxy, ethoxy, n-propoxy, isopropoxy and n-butoxy;

(d) Halo(lower)alkyl includes (lower)alkyl radicals as defined under (b) where one or more hydrogen atoms are substituted by halogen as defined under (a). Examples include $—CF_3$, $—CCl_3$, $—CH_2Cl$, $—CHCl_2$, $—CH_2CH_2Cl$, $—CH_2CF_3$, $—CH_2CH_2CHClCH_3$ or $—CH_2CHClCH_2CH_3$; and (e) The phenyl and naphthyl groups above may be optionally substituted by one, two or three nonhydrogen substituents at any of the available positions of the ring system. The naphthyl radical may be either the α- or β-isomer. Preferred aryl radicals are those which are unsubstituted or which have one non-hydrogen substituent.

As denoted by the structural formulae provided above, the compounds of formulae II and III all have the 3-hydroxy substituent in the α-configuration. Additionally, the compounds of formulae I–III all have the β-configuration at the 4-substituent. Compounds of formula III may exist in the form of the 8α- and 8β-hydroxy epimers or mixtures thereof, but the present invention is specifically limited to the 8β epimer of the compound where $R^1$=$R^2$=methyl. Certain compounds within the scope of formulae I–III contain asymmetric carbon atoms (e.g. when $R^1$ and $R^2$ are butyl) and, in such cases, the compounds may exist in the form of the individual optical isomers as well as the racemates.

The compounds of formula I may be prepared by reacting the appropriate diol intermediate of formula III with about two equivalents of a suitable oxidizing agent in an inert organic solvent.

In general any oxidizing agent capable of converting a sterically hindered hydroxyl group to a carbonyl group may be employed in the above process. A particularly preferred reagent is dimethyl sulfoxide-trifluoroacetic anhydride (DMSO-TFAA) which is described in *J. Org. Chem.* 41(20): 3329 (1976). This reagent may be conveniently used in a dry inert organic solvent such as methylene chloride or tetrahydrofuran at temperatures of from about −78° C. to −50° C. Upon addition of the reagent to the diol intermediate III, a dimethylalkoxysulfonium salt is formed which on treatment with base (e.g. triethylamine) is rapidly converted in good yield to the corresponding diketo product I. An alternative preferred oxidizing reagent is dimethylsulfoxide-acetic anhydride. This oxidizing agent is employed in a similar manner as DMSO-TFAA except that the reaction is preferably carried out at about room temperature.

Compounds of formula I may also be prepared from the appropriate 8-keto intermediate of formula II by oxidation with about one equivalent of a suitable oxidizing agent such as dimethyl sulfoxide-trifluoroacetic anhydride, dimethylsulfoxide-acetic anhydride or N-chlorosuccinimide dimethylsulfide in an inert organic solvent such as methylene chloride or toluene. The preferred temperature conditions for this reaction are about −78° to −50° C. for dimethyl sulfoxidetrifluoroacetic anhydride, room temperature for dimethylsulfoxide-acetic anhydride and 0° C. for N-chlorosuccinimide dimethyl sulfide.

Other reaction temperatures may be successfully employed in the oxidations of compounds II and III, but product yields may be reduced from those achieved under the preferred conditions.

The 8-keto intermediate of formula II may be prepared by selective oxidation of the 8-hydroxy group of the appropriate diol compound of formula III in an inert organic solvent such as dioxane, acetone or methylene chloride. Mild oxidizing agents are used in this conversion such as manganese dioxide, 2,3-dichloro-5,6-dicyano-1,4-benzoquinone or pyridinium chlorochromate. The most preferred oxidizing agent for this step is pyridinium chlorochromate. Advantageous results are obtained with this reagent when the oxidation reaction is carried out at about room temperature in an acetate-buffered methylene chloride solvent (see *Tetrahedron Letters* 31:2647–2650 (1975) for further details of the procedure).

Diol intermediates of formula III may be prepared from the appropriate 3α-hydroxy ester of the formula

IV

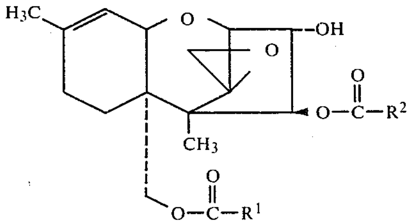

by selectively oxidizing ester IV in an inert solvent so as to introduce an 8-hydroxy group. A preferred oxidizing agent is selenium dioxide which may be conveniently reacted with ester IV in aqueous dioxane at reflux temperature.

Alternatively, the 8-hydroxy group of intermediate III may be introduced on the appropriate ester of formula IV by subjecting ester IV to N-bromosuccinimide bromination in an inert organic solvent such as methylene chloride and then displacing the 8-bromo group with aqueous base in the presence of a silver salt such as silver trifluoroacetate.

Starting material 3α-hydroxy esters of general formula IV are known in the art or are prepared by methods well-known to those skilled in the art. Examples of suitable methods are provided below under "Preparation of Starting Materials", but in general the esters may be prepared as shown in the following schemes:

-continued

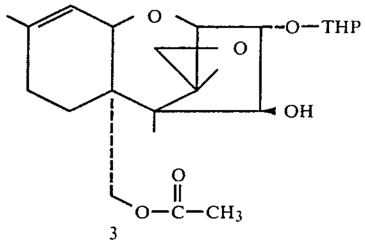

3

Scheme I

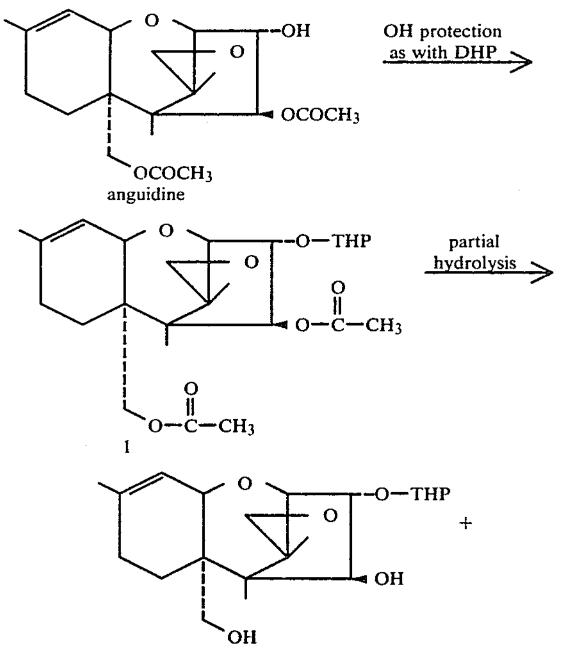

anguidine

1

2

Scheme II ($R^1=R^2$)

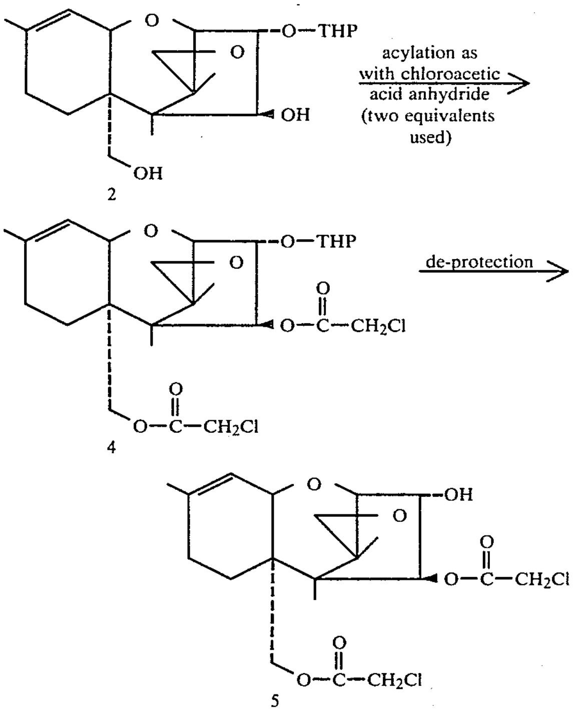

2

4

5

Scheme III ($R^1 \neq R^2$)

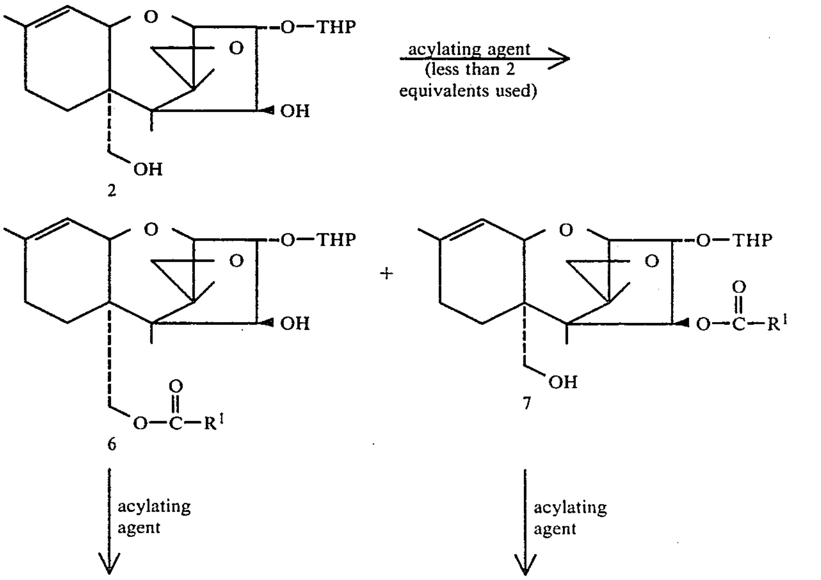

2

6

7

-continued

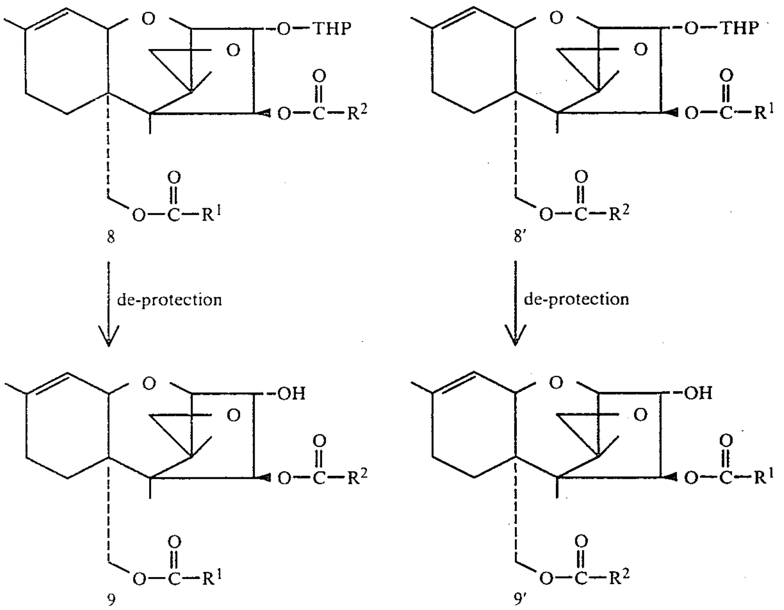

8 8' 9 9'

EXPLANATION OF SCHEMES I-III

Using anguidine as the starting material, other 4β,15-diacylated esters of formula IV may be prepared by protecting the 3-OH group as by conversion to a tetrahydropyranyl ether (1), and then subjecting the 3α-THP derivative to partial basic hydrolysis to give a mixture of the 4-OH (3) and 4,15-OH (2) derivatives.

Compound 2 may then be acylated in accordance with conventional methods with about two equivalents of a suitable acylating derivative of a carboxylic acid R—COOH to produce a 4,15-diacylated derivative 4 which may then be de-protected to give 5. The acylation is typically carried out with an acid halide or acid anhydride, preferably in the presence of an organic base such as pyridine or lutidine. Scheme II results in formation of a 4,15-diacylated ester of general formula IV having $R^1=R^2$.

To prepare esters of formula IV where $R^1 \neq R^2$, the 4,15-diol 2 may be acylated with less than two equivalents of acylating agent to give a mixture of monoacylated derivatives 6 and 7 as shown in Scheme III. These derivatives can be separated chromatographically and then treated with a second acylating agent to give the diacylated derivatives 8 and 8'. Upon de-protection the products 9 and 9' containing mixed acyl groups are produced.

Mixed diacylated esters of formula IV where $R^1$ is methyl may also be prepared by acylation and de-protection of compound 3.

BIOLOGICAL ACTIVITY

Representative compounds of the present invention were tested for antitumor activity against the transplantable mouse tumors P-388 leukemia, L-1210 leukemia and Lewis Lung carcinoma and the results of these tests are shown below in Tables I-VI. The methodology used generally followed the protocols of the National Cancer Institute [see, for example, *Cancer Chemotherapy Rep., Part* 3, 3:1-103 (1972)]. The essential experimental details are give at the bottom of the tables.

Table I

Effect of Compound of Example 1 on P-388 Leukemia

| Material | Dose mg/kg | MST Days | Effect MST % T/C | Average Weight Change,g | Survivors Day 5 |
|---|---|---|---|---|---|
| Anguidine | 1.6 | 15.5 | 172 | +1.0 | 6/6 |
| | 0.8 | 14.5 | 161 | +0.6 | 6/6 |
| | 0.4 | 13.0 | 144 | −0.6 | 6/6 |
| | 0.2 | 12.0 | 133 | −1.3 | 6/6 |
| | 0.1 | 10.0 | 117 | +0.5 | 6/6 |
| | 0.05 | 10.0 | 111 | +0.6 | 6/6 |
| Compound of Example 1 | 6.4 | Tox | Tox | Tox | 0/6 |
| | 3.2 | Tox | Tox | Tox | 1/6 |
| | 1.6 | Tox | Tox | Tox | 1.6 |
| | 0.8 | 15.0 | 167 | −0.8 | 5/6 |
| | 0.4 | 14.0 | 156 | +0.3 | 6/6 |
| | 0.2 | 12.0 | 133 | +0.7 | 6/6 |
| | 0.1 | 12.0 | 133 | +0.7 | 6/6 |
| | 0.05 | 10.0 | 111 | +0.9 | 6/6 |
| Control | Saline | 9.0 | — | +2.4 | 10/10 |

Tumor inoculum: $10^6$ ascites cells implanted i.p.
Host: $CDF_1$ ♀ mice.
Treatment: Once daily for 9 days starting day 1
Evaluation: MST = median survival time.
Effect: % T/C = (MST treated/MST control) × 100.
Criteria: T/C ≧ 125 considered significant antitumor activity.

Table II

Effect of Compound of Example 3 on L-1210 Leukemia

| Material | Dose, IP mg/kg/day | MST Days | Effect MST % T/C | Average Weight Change,g | Survivors Day 5 (30) |
|---|---|---|---|---|---|
| Anguidine | 2.0 | 11.0 | 157 | −0.8 | 6/6 |
| NSC 141537 | 1.6 | 11.0 | 157 | −0.3 | 6/6 (1/6) |
| | 1.2 | 11.0 | 157 | −0.3 | 6/6 |
| | 0.8 | 11.0 | 157 | −0.3 | 6/6 |
| | 0.4 | 10.0 | 143 | −0.1 | 6/6 |
| | 0.2 | 9.0 | 129 | +0.5 | 6/6 (1/6) |
| Compound of Example 3 | 2.0 | 9.0 | 129 | −1.6 | 3/6 |
| | 1.6 | 16.5 | 236 | −1.3 | 6/6 |
| | 1.2 | 13.5 | 193 | −1.9 | 6/6 |
| | 0.8 | 12.0 | 171 | −1.0 | 6/6 |
| | 0.4 | 11.5 | 164 | −0.9 | 6/6 (1/6) |
| | 0.2 | 11.0 | 157 | −0.5 | 6/6 |
| | 0.1 | 8.0 | 114 | −0.6 | 6/6 (1/6) |

Table II-continued

| Effect of Compound of Example 3 on L-1210 Leukemia | | | | | |
|---|---|---|---|---|---|
| Material | Dose, IP mg/kg/day | MST Days | Effect MST % T/C | Average Weight Change,g | Survivors Day 5 (30) |
| Control | Saline | 7.0 | — | +0.9 | 10/10 |

Tumor inoculum : $10^6$ ascites cells implatned ip
Host : $BDF_1$ ♀ mice.
Treatment : Once daily for 9 days starting day 1
Tox : <4/6 mice alive on Day 5
Evaluation : MST = median survival time.
Effect : % T/C = (MST treated/MST control) × 100.
Criteria : % T/C ≧ 125 considered significant antitumor activity.

Table III

| Effect of Compound of Example 3 on P-388 Leukemia | | | | | |
|---|---|---|---|---|---|
| Material | Dose mg/kg/day | MST Days | Effect MST % T/C | Average Weight Change,g | Survivors Day 5 |
| Anguidine | 1.6 | 16.0 | 178 | +1.3 | 6/6 |
| NSC 141537 | 0.8 | 15.0 | 167 | −0.5 | 6/6 |
| | 0.4 | 13.0 | 144 | +0.6 | 6/6 |
| | 0.2 | 12.0 | 133 | +0.2 | 6/6 |
| | 0.1 | 12.0 | 133 | +0.9 | 6/6 |
| | 0.05 | 11.0 | 122 | +0.9 | 6/6 |
| Compound of Example 3 | 6.4 | 8.0 | 89 | −0.7 | 3/6 |
| | 3.2 | 14.5 | 161 | −2.5 | 4/6 |
| | 1.6 | 22.5 | 250 | −0.9 | 6/6 |
| | 0.8 | 17.0 | 189 | +0.2 | 6/6 |
| | 0.4 | 14.5 | 161 | −0.2 | 6/6 |
| | 0.2 | 13.5 | 150 | −1.0 | 6/6 |
| | 0.1 | 12.5 | 139 | −0.3 | 6/6 |
| | 0.05 | 12.0 | 133 | −1.5 | 6/6 |
| Control | Saline | 9.0 | — | +0.8 | 10/10 |

Tumor inoculum : $10^6$ ascites cells implanted i.p.
Host : $CDF_1$ ♂ mice.
Treatment : Once daily for 9 days starting day 1
Tox : <4/6 survivors Day 5.
Evaulation : MST = median survival time
Effect : % T/C = (MST treated/MST control) × 100.
Criteria : % T/C ≧ 125 considered significant antitumor activity.

Table IV

| Effect of Compound of Example 3 on P-388 Leukemia (repeat test) | | | | | | |
|---|---|---|---|---|---|---|
| Material | Treat-ment | Dose mg/kg/inj | MST Days | Effect MST % T/C | Average Weight Change,G | Sur-vivors Day 5 (30) |
| Anguidine | Days 1→9 | 2.0 | 16.0 | 178 | +0.5 | 6/6 |
| | | 1.6 | 16.5 | 183 | +0.3 | 6/6 |
| | | 1.2 | 15.5 | 172 | +0.9 | 6/6 |
| | | 0.8 | 14.0 | 156 | +0.7 | 6/6 |
| Compound of Example 3 | Days 1→9 | 2.0 | 10.0 | 111 | −0.3 | 6/6 |
| | | 1.6 | 27.5 | 306 | +0.1 | 6/6 (2) |
| | | 1.2 | 19.5 | 217 | +0.8 | 6/6 |
| | | 0.8 | 19.5 | 217 | −0.1 | 6/6 |
| | Day 1 only | 10.0 | 13.5 | 150 | −1.8 | 4/6 |
| | | 7.0 | 12.5 | 139 | −0.6 | 4/4 |
| Control | | Saline | 9.0 | — | +1.0 | 10/10 |

Tumor inoculum : $10^6$ ascites cells implanted i.p.
Host : $CDF_1$ ♂ mice.
Treatment : Once daily for 9 days starting day 1
Tox : <4/6 survivors Day 5.
Evaulation : MST = median survival time
Effect : % T/C = (MST treated/MST control) × 100.
Criteria : % T/C ≧125 considered significant antitumor activity.

Table V

| Effect of Compound 5 on P-388 Leukemia | | | | | |
|---|---|---|---|---|---|
| Material | Dosage, IP mg/kg/inj | MST Days | Effect MST % T/C | Average Weight Change,g | Survivors Day 5(30) |
| Anguidine | 1.6 | 16.0 | 200 | +0.9 | 6/6 |
| NSC 141537 | 0.8 | 14.0 | 175 | +1.6 | 6/6 |
| | 0.4 | 13.0 | 163 | +1.6 | 6/6 |
| | 0.2 | 12.0 | 150 | +0.9 | 6/6 |
| Compound of Example 5 | 6.4 | TOX | TOX | TOX | 2/6 |
| | 3.2 | 8.0 | 100 | −0.9 | 5/6 |
| | 1.6 | 21.5 | 270 | 0 | 6/6 (1) |
| | 0.8 | 18.5 | 231 | +0.3 | 6/6 |
| | 0.4 | 15.5 | 194 | +0.6 | 6/6 |
| | 0.2 | 12.0 | 150 | +0.4 | 6/6 |
| | 0.1 | 12.5 | 156 | +0.5 | 6./6 |
| | 0.05 | 12.0 | 150 | +0.1 | 5/6 |
| Control | Saline | 8.0 | — | +1.8 | 10/10 |

Tumor inoculum : $10^6$ ascites brei cells implanted ip.
Host : $CDF_1$ ♀ mice.
Treatment : Once daily for 9 days starting day 1
Tox : <4/6 mice alive on Day 5.
Evaluation : MST = median survival time.
Effect : % T/C = (MST treated/MST control) × 100.
Criteria : % T/C ≧ 125 considered significant antitumor activity.

Table VI

| Effect of Trichothecene Derivatives on Lewis Lung Carcinoma | | | | | |
|---|---|---|---|---|---|
| Material | Dose, IP mg/kg/day | MST Days | Effect MST % T/C | Average Weight Change | Survivors Day 5(60) |
| Anguidine | 1.6 | 21.0 | 124 | +2.2 | 10/10 |
| NSC 141537 | 0.8 | 21.0 | 124 | +1.8 | 10/10 |
| | 0.4 | 23.0 | 135 | +1.4 | 10/10 |
| Compound of | 2.0 | 30.0 | 176 | +0.3 | 10/10 |
| Example 5 | 1.5 | 31.0 | 182 | +0.8 | 10/10 |
| | 1.0 | >60.0 | >353 | +1.0 | 10/10 (5) |
| | 0.5 | >60.0 | >353 | +1.6 | 10/10 (5) |
| Control | Saline | 17.0 | — | −0.6 | 10/10 |

Tumor inoculum : $10^6$ tumor brei cells, ip.
Host : $BDF_1$ ♂ mice.
Treatment : QD 1→9.
Tox : <6/10 mice alive on Day 5.
Evaluation : MST = median survival time.
Effect : % T/C = (MST treated/MST control) × 100.
Criteria : % T/C ≧ 125 considered significant antitumor activity.

Analysis: The compound of Example 1 has an optimum dose (O.D.) of 0.8 mg/kg/day vs. 1.6 mg/kg/day for anguidine. This compound thus has twice the potency of anguidine.

The compound of Example 3 has approximately the same potency as anguidine but is clearly superior in causing prolonged survival of mice bearing L-1210 leukemia and in repeated tests with P-388 leukemia.

The compound of Example 5 is about equal in potency to anguidine and causes greater survival increases in tests on P-388 leukemia and Lewis Lung carcinoma.

The experimental animal tests described above demonstrate that the compounds of the present invention possess marked inhibitory action against mammalian malignant tumors. While all of the compounds included within the scope of formulae I-III possess antitumor activity, the most preferred compounds for therapeutic use are the compounds of formula I. Compounds of formulae II and III, therefore, are of most importance as intermediates for preparation of the preferred compounds I.

According to another aspect of this invention, therefore, there is provided a method for therapeutically treating a mammalian host affected by a malignant tumor which comprises administering to said host an effective tumor-inhibiting dose of a compound of formula I, II or III.

In yet another aspect of the invention, a pharmaceutical composition is provided which comprises an effective tumor-inhibiting amount of a compound of formulae I-III in combination with an inert pharmaceutically acceptable carrier or diluent. These compositions may be made up in any pharmaceutical form appropriate for parenteral administration.

Preparations according to the invention for parenteral administration include sterile aqueous or nonaqueous solutions, suspensions or emulsions. They may also be manufactured in the form of sterile solid compositions which can be dissolved in sterile water, physiological saline or some other sterile injectable medium immediately before use.

It will be appreciated that the actual preferred dosages of the compounds of the present invention will vary according to the particular compound being used, the particular composition formulated, the mode of administration and the particular situs, host and disease being treated. Many factors that modify the action of the drug will be taken into account by those skilled in the art, e.g. age, body weight, sex, diet, time of administration, route of administration, rate of excretion, condition of the host, drug combinations, reaction sensitivities and severity of the disease. Optimal dosages for a given set of conditions can be ascertained by those skilled in the art using conventional dosage determination tests in view of the experimental animal data provided, the available data on clinical use of anguidine and the above-mentioned guidelines.

The following examples are not limiting but are intended to be illustrative of this invention. SKELLYSOLVE B is a commercially available petroleum solvent (Skelly Oil Co.) comprising isomeric hexanes and having a boiling point of 60°-68° C. The main component of Skellysolve B is n-hexane. Unless otherwise indicated, all temperatures below are in degrees Celsius and all solvent percentages are by volume.

PREPARATION OF STARTING MATERIALS

Preparation 1

4β,15-Diacetoxy-3α-O-(2′-tetrahydropyranyl)-12,13-epoxytrichothec-9-ene

A mixture of 4β,15-diacetoxy-3α-hydroxy-12,13-epoxytrichothec-9-ene (12.81 g, 35 mmol), 2,3-dihydro-4H-pyran (17.5 ml, 189 mmol), and p-toluenesulfonic acid (70 mg, 0.35 mmol) in 150 ml of $CH_2Cl_2$ was stirred at room temperature for 2 h. After addition of 2.1 g of $K_2CO_3$, the reaction mixture was diluted with 400 ml of $CH_2Cl_2$ and washed with saturated $NaHCO_3$ solution and brine. Drying over $K_2CO_3$ and removal of the solvent gave a colorless oil which crystallized slowly from petroleum ether to give 11.30 g (72%) of solid. m.p. 93°-94° C.; IR(KBr): 2976, 1746, 1249, 1080, 1040, 988 $cm^{-1}$.

Anal. Calc'd for $C_{24}H_{34}O_8$: C, 63.98; H, 7.61. Found: C, 64.35; H, 7.58.

Preparation 2

3α,4β,15-trihydroxy-12,13-epoxytrichothec-9-ene

4β,15-diacetoxy-3α-hydroxy-12,13-epoxytrichothec-9-ene (15 g) was stirred for 20 minutes in 300 ml of methanol with 900 ml of 0.3 N sodium hydroxide (Sigg et al. Helv. Chim. Acta, 48, 962–988 (1965). The solution was placed on a column containing 1 kg of DOWEX 50 (H+ cycle) prepared with 20% methanol in water. The column was eluted with 3 l of the same solvent, the eluate concentrated, and the residual aqueous solution freeze-dried. The powder was dissolved in methanol, mixed with 10 g of silica gel, and dried in vacuo. The dry silica gel mixture was placed on a column of fresh silica gel (2.5×100 cm) and eluted with methylene chloride with increasing amounts of methanol. Fractions appearing homogeneous on TLC plates were dried and crystallized from ethyl acetate. Yield: 7.3 g, m.p. 194°-195° C. IR(KBr): 3490, 3450, 3390, 2990-2900 (four peaks), 1675, 960 and 950 $cm^{-1}$. $[\alpha]_D^{22}=-15.4°$ (c=1, acetone).

Anal. Calc'd for $C_{15}H_{22}O_6$: C, 63.81; H, 7.86. Found: C, 63.71; H, 7.80.

Alternatively, the 3-O-tetrahydropyranyl derivative (Preparation 3 below) (1 g) was stirred for four hours in 115 ml of 95% ethanol and 23 ml of 1 N HCl. The solution was azeotropically distilled with the addition of absolute ethanol, the concentrated ethanolic solution diluted with diethyl ether, and the resulting title product crystallized from ethyl acetate as a gum.

Preparation 3

4β,15-Dihydroxy-3α-O-(2′-tetrahydropyranyl)-12,13-epoxytrichothec-9-ene

To a solution of 4β,15-diacetoxy-3-O-(2′-tetrahydropyranyl)-12,13-epoxytrichothec-9-ene (1.067 g, 2.37 mmol) in 40 ml of tetrahydrofuran and methanol (5:3 v/v) was added 20 ml of 0.3 N NaOH solution. After 2.5 h of stirring at room temperature, an additional 20 ml of 0.3 N NaOH solution was introduced, and stirring was continued for 18.5 h. The resulting solution was diluted with $CH_2Cl_2$ (200 ml) and washed with water. The aqueous layer was reextracted with $CH_2Cl_2$ (2×50 ml). The combined $CH_2Cl_2$ layers were washed with brine and dried over $K_2CO_3$. Removal of the solvent gave 891 mg of foam, which was subsequently chromatographed on silica gel. Elution with 1% methanol-$CH_2Cl_2$ gave 46 mg (5%) of 15-acetoxy-4β-hydroxy-3α-O-(2′-tetrahydropyranyl)-12,13-epoxytrichothec-9-ene. A further elution with 5% methanol-$CH_2Cl_2$ gave 808 mg (93%) of the title compound as an amorphous solid. IR(KBr): 3457, 2943, 1445, 1135, 1125, 1078, 1035, 1020, 978, 957 $cm^{-1}$.

Preparation 4

15-Acetoxy-4β-hydroxy-3α-O-(2′-tetrahydropyranyl)-12,13-epoxytrichothec-9-ene To a solution of 4β,15-diacetoxy-3α-O-(2′-tetrahydropyranyl)-12,13-epoxytrichothec-9-ene (31.14 g, 69.2 mmol) in 800 ml of methanol and tetrahydrofuran (1:1 v/v) was added 400 ml of 1.31 N $NH_4OH$ solution. After 3 days stirring at room temperature, 10 ml of concentrated $NH_4OH$ solution was added to the reaction mixture. Stirring was continued for an additional 4 days. The volume of the resulting solution was reduced to 500 ml. Extraction with $CH_2Cl_2$, washing with brine, and removal of the solvent gave 37 g of a slightly yellow oil. Chromatography on silica gel (elution with 1% methanol-$CH_2Cl_2$) gave 10.65 g (38%) of the title compound as an oil. The NMR and IR spectra of this material were consistent with the structure of the title compound. IR(KBr): 3430, 2970, 2950, 2875, 1744, 1720, 1270, 1248, 1126, 1080, 1040, 972 $cm^{-1}$.

Preparation 5

4β,15-Bis-(2'-bromoacetoxy)-3α-hydroxy-12,13-epoxy-trichothec-9-ene

A solution containing 183 mg (0.5 mmol) of 3α-O-(2'-tetrahydropyranyl)-4β,15-dihydroxy-12,13-epoxytrichothec-9-ene and 268 mg (2.5 mmol) of 2,6-lutidine was cooled to 5° C. To this solution was added with stirring 253 mg (1.25 mmol) of bromoacetyl bromide and the resulting solution was kept without cooling for 18 h. The usual work-up gave a gum which was dissolved in 36 ml of 95% ethanol and 6 ml of 1 N HCl and stored for 20 h at 22° C. The usual work-up gave a foam which was chromatographed on 20 g of silica gel (Mallinckrodt SILICAR CC-7) using 1% methanol in $CH_2Cl_2$ as the solvent. The product eluted as a pale yellow band which gave a foam on evaporation of the solvent. Crystallization from diethyl ether afforded a colorless solid of m.p. 125°-126°. IR(KBr): 3480, 2960, 1750, 1735, 1280, 1165 $cm^{-1}$.

Anal. Calc'd for $C_{19}H_{24}Br_2O_7$: C, 43.53; H, 4.61. Found: C, 45.47; H, 4.84.

Preparation 6

4β,15-Bis(chloroacetoxy)-3α-O-(2'-tetrahydropyranyl)-12,13-epoxytrichothec-9-ene A mixture of 4β,15-dihydroxy-3α-O-(2'-tetrahydropyranyl)-12,13-epoxytrichothec-9-ene (808 mg, 2.21 mmol), chloroacetic anhydride (1.132 g, 6.62 mmol) and pyridine (894 mg, 11.05 mmol) in 100 ml of $CH_2Cl_2$ was stirred at room temperature for 14 h. The reaction mixture was diluted with 200 ml of $CH_2Cl_2$ and washed with saturated $NaHCO_3$ solution, 1% HCl solution and brine. Drying over $K_2CO_3$ and removal of the solvent gave 1.058 g (92%) of foam which was homogeneous on TLC. A portion of this material was purified by silica gel chromatography (elution with 0.5% methanol-$CH_2Cl_2$) to furnish an analytical sample of title product. IR(KBr): 2955, 1762, 1740, 1290, 1186, 1172, 1129, 1080, 1039, 977 $cm^{-1}$.

Preparation 7

4β,15-Bis(chloroacetoxy)-3α-hydroxy-12,13-epoxytrichothec-9-ene

To a solution of 4β,15-bis(chloroacetoxy)-3α-O-(2'-tetrahydropyranyl)-12,13-epoxytrichothec-9-ene (858 mg, 1.65 mmol) in 100 ml of 95% ethanol was added 19 ml of 1 N HCl solution. The resulting solution was stirred at room temperature for 24 hours. The reaction mixture was diluted with $CH_2Cl_2$ (300 ml) and washed with saturated $NaHCO_3$ solution and brine. Drying over $K_2CO_3$-$Na_2SO_4$ and removal of the solvent gave 600 mg of foam. Chromatography of this material on silica gel (elution with 1% methanol-$CH_2Cl_2$) gave 524 mg (73%) of 4β,15-bis(chloroacetoxy)-3α-hydroxy-12,13-epoxytrichothec-9-ene. An analytical sample was obtained by recrystallization from chloroform-diethyl ether, m.p. 139°-141° C. IR(KBr): 3450, 2970, 2913, 1758, 1742, 1327, 1293, 1192, 1173, 1083, 1008, 967 $cm^{-1}$. Elution of the silica gel column with 2% methanol-$CH_2Cl_2$ gave 110 mg (15%) of 15-chloroacetoxy-3α,4β-dihydroxy-12,13-epoxytrichothec-9-ene.

Anal. Calc'd. for $C_{19}H_{24}O_7Cl_2$: C, 52.42; H, 5.56. Found: C, 52.31; H, 5.34.

Preparation 8

15-Acetoxy-4β-chloroacetoxy-3α-hydroxy-12,13-epoxytrichothec-9-ene

A mixture of 15-acetoxy-4β-hydroxy-3α-O-(2'-tetrahydropyranyl)-12,13-epoxytrichothec-9-ene (785 mg, 1.92 mmol), chloroacetic anhydride (492 mg, 2.88 mmol) and pyridine (0.309 ml, 3.84 mmol) in 100 ml of $CH_2Cl_2$ was stirred at room temperature for 28.5 h. The reaction mixture was diluted with $CH_2Cl_2$ (200 ml) and washed with saturated $NaHCO_3$ solution and brine. Drying over $K_2CO_3$ and removal of the solvent gave 931 mg (100%) of a white foam. The NMR and IR spectra of this material were consistent with the structure of 15-acetoxy-4β-chloroacetoxy-3α-O-(2'-tetrahydropyranyl)-12,13-epoxytrichothec-9-ene.

To a solution of 15-acetoxy-4β-chloroacetoxy-3α-O-(2'-tetrahydropyranyl)-12,13-epoxytrichothec-9-ene (900 mg, 1.98 mmol) in 100 ml of 95% ethanol was added 19 ml of 1 N HCl solution. After 10 h of stirring at room temperature, 200 ml of $CH_2Cl_2$ was added to the reaction mixture. The aqueous layer which separated was extracted with 25 ml of $CH_2Cl_2$. The combined $CH_2Cl_2$ layers were washed with saturated $NaHCO_3$ solution and brine. Drying over $K_2CO_3Na_2SO_4$ and removal of the solvent gave 662 mg of foam. Chromatography on silica gel (elution with 0.5% methanol-$CH_2Cl_2$) gave 350 mg (44%) of the title compound. Recrystallization from diethyl ether furnished the analytical sample; m.p. 166°-167.5° C. IR(KBr): 3500, 3040, 3020, 2989, 2918, 1754, 1736, 1378, 1330, 1260, 1208, 1167, 1074, 1052, 960 $cm^{-1}$.

Anal. Calc'd for $C_{19}H_{25}O_7Cl$: C, 56.83; H, 6.29. Found: C, 57.12; H, 6.29.

Preparation 9

4β,15-Diacetoxy-3-hydroxy-12,13-epoxytrichothec-9-en-8-one

A mixture of 4β,15-diacetoxy-3α,8β-dihydroxy-12,13-epoxytrichothec-9-ene (270 mg, 0.71 mmol), pyridium chlorochromate (2.23 mg, 1.03 mmol), and anhydrous sodium acetate (29 mg, 0.35 mmol) in 15 ml of $CH_2Cl_2$ was stirred at room temperature for 2.5 h. After filtration through CELITE, the solvent was removed under reduced pressure to give 360 mg of oil. Chromatography on silica gel (elution with 0.75% methanol-$CH_2Cl_2$) gave 218 mg (81%) of foam which was homogeneous on TLC (thin layer chromatography). IR (KBr): 3445, 2980, 2920, 1740, 1678, 1366, 1240, 1042 $cm^{-1}$.

Anal. Calc'd for $C_{19}H_{24}O_8$: C, 59.99; H, 6.36. Found: C, 59.36; H, 6.41.

Preparation 10

15-(trans-2'-butenoyloxy)-3α,4β-dihydroxy-12,13-epoxytrichothec-9-ene

A solution containing 366 mg (1 mmol) of 3α-O-(2'-tetrahydropyranyl)-4β,15α-dihydroxy-12,13-epoxytrichothec-9-ene and 395 mg (5 mmol) of dry pyridine in 50 ml of $CH_2Cl_2$ (previously dried over 4 Å molecular sieves) was cooled at 5° C. To the stirred solution was added dropwise 261 mg (2.5 mmol) of trans-2-butenoic acid chloride and, after completion of the addition, the mixture was stirred for 1 h at 5° C. and for 16 h at ambient temperature. The solution was diluted with 50 ml of $CH_2Cl_2$ and was successively washed with saturated aqueous $NaHCO_3$, brine, 1% aqueous HCl and brine. The organic phase was dried over $Na_2SO_4$ and the solvent was evaporated under reduced pressure to provide 360 mg of a gum. This was dissolved in 50 ml of 95% ethanol and to it was added 5 ml of 2 N HCl. After the solution had been stored at room temperature for 22 h, it was diluted with 100 ml of $CH_2Cl_2$ and was washed successively with $H_2O$, saturated aqueous $NaHCO_3$ and brine. The organic phase was dried over $Na_2SO_4$ and the solvent was evaporated under reduced pressure to provide 260 mg of gum. This was chromatographed on 20 g of silica gel (Mallinckrodt SILICAR CC-7) using 1% methanol in $CH_2Cl_2$ as the solvent. The first product eluted was the bis-ester (26 mg) (Preparation 11) followed by 22 mg of the 4-monoester (Preparation 11) and then 147 mg of the title compound which was crystallized from $CHCl_3$-SKELLYSOLVE B as a white solid of m.p. 83°-86° C. IR(KBr): 3440, 2970, 1725, 1190, 1110, 1085, 965 $cm^{-1}$.

Anal. Calc'd for $C_{19}H_{26}O_6.0.5H_2O$: C, 63.49; H, 7.57. Found: C, 63.54; H, 7.43.

Preparation 11

4β,15-Bis-(trans-2'-butenoyloxy)-3α-hydroxy-12,13-epoxytrichothec-9-ene

Repetition of the above experiment using 6 equivalents of trans-2-butenoic acid chloride gave the title compound as a hygroscopic white foam. IR(KBr): 3420, 2970, 1720, 1310, 1260, 1185, 965 $cm^{-1}$. In addition, there was obtained 4β(trans-2'-butenoyloxy)-3α,15-dihydroxy-12,13-epoxytrichothec-9-ene as a cream solid of m.p. 60°-62° C. IR(KBr): 3460, 2960, 1710, 1315, 1190, 1105, 1080, 955 $cm^{-1}$.

Anal. Calcd for $C_{19}H_{26}O_6$.: C, 64.30; H, 7.53. Found: C, 64.19; H, 8.06.

Preparation 12

15-(2'-Methylpropenoyloxy)-3α,4β-dihydroxy-12,13-epoxytrichothec-9-ene

To a solution of 366 mg (1 mmol) of 3α-O-(2'-tetrahydropyranyl)-4β,15-dihydroxy-12,13-epoxytrichothec-9-ene and 395 mg (5 mmol) of dry pyridine in 50 ml of methylene chloride (dried over 4Å molecular sieves) was added with stirring 261 mg (2.5 mmol) of freshly distilled 2-methylpropenoic acid chloride. The solution was stored at 22° C. for 17 h and was then treated with an additional 261 mg (2.5 mmol) of the acid chloride. After a further 22 h at 22° C., the solution was worked up as described in Preparation 10 and the residue was chromatographed on 20 g of silica (Mallinckrodt SILICAR CC-7). 2-Methylpropenoic acid anhydride was eluted using 1% methanol in $CH_2Cl_2$. The solvent was changed to methanol to elute 230 mg of white foam which was hydrolyzed as described above (Preparation 10) to give 189 mg of a foam. This was chromatographed on 20 g silica (Mallinckrodt SILICAR CC-7) using 1% methanol in $CH_2Cl_2$ as the solvent. Minor products were eluted and the solvent was changed to 20% methanol in $CH_2Cl_2$ to afford 116 mg (33%) of the title compound as a foam which crystallized from $CH_2Cl_2$-SKELLYSOLVE B as a pale pink solid of m.p. 79°-81° C. IR(KBr): 3440, 2960, 1715, 1165, 1080, 955 $cm^{-1}$.

Anal. Calc'd for $C_{19}H_{26}O_6.0.5H_2O$: C, 63.49; H, 7.57. Found: C, 63.36; H, 7.40.

Preparation 13

4β,15-Bis-(2'-methylpropenoyloxy)-3α-hydroxy-12,13-epoxytrichothec-9-ene

A solution containing 3.66 g (0.01 mol) of 3α-O-(2'-tetrahydropyranyl)-4β,15-dihydroxy-12,13-epoxytrichothec-9-ene, 3.95 (0.05 mol) of pyridine and 2.61 g (0.025 mol) of freshly distilled 2-methylpropenoic acid chloride in 250 ml of dry methylene chloride was stirred for 16 h at 22° C. An additional 2.61 g (0.025 mol) of the acid chloride was added and stirring was continued for 6 h. The solution was diluted with $CH_2Cl_2$ and was washed in succession with saturated aqueous $NaHCO_3$, brine, 1% aqueous HCl and brine. The organic phase was dried over $Na_2SO_4$ and the solvent evaporated under reduced pressure to give 5.36 g of an oil. This was chromatographed on 100 g of silica gel (Mallinckrodt SILICAR CC-7) using 1% methanol in $CH_2Cl_2$ as the solvent. Methacrylyl anhydride was first eluted, followed by 615 mg of a foam which was hydrolysed as before (Preparation 10) in 67.5 ml of 95% ethanol and 13.5 ml of 1 N HCl. The usual work-up gave 590 mg of gum from which, by chromatography, 198 mg of the title compound was isolated as a hygroscopic foam IR(KBr): 3500, 2960, 1720, 1165, 1080, 960 $cm^{-1}$; which was identified by its NMR spectrum. The next fraction from this chromatography afforded 4β-(2'-methylpropenoyloxy)-3α,15-dihydroxy-12,13-epoxytrichothec-9-ene as colorless crystals of m.p. 175°-176° C. IR(KBr): 3510, 3460, 2500, 1690, 1330, 1300, 1170, 1080, 1060, 910, 900 $cm^{-1}$.

Anal. Calc'd for $C_{19}H_{26}O_6.0.25H_2O$: C, 64.30; H, 7.53. Found: C, 64.24; H, 7.14.

From the chromatographic separation of the tetrahydropyranyl ethers (above) there was next obtained 810 mg of a foam which was re-chromatographed on fresh silica gel (20 g) using the same solvent system to provide 3α-O-[2'-tetrahydropyranyl]-15-(2'-methylpropenoyloxy)-4β-hydroxy-12,13-epoxytrichothec-9-ene as a foam.

Preparation 14

4β-(2'-Chloroacetoxy)-15-(2'-methylpropenoyloxy)-3α-hydroxy-12,13-epoxytrichothec-9-ene To a stirred solution of 164 mg (0.38 mmol) of 3α-O-(2'-tetrahydropyranyl)-15-(2'-methylpropenoyloxy)-4β-hydroxy-12,13-epoxytrichothec-9-ene (Preparation 13) in 25 ml of dry $CH_2Cl_2$ were added in succession 36 mg (0.46 mmol) of pyridine and 78 mg (0.46 mmol) of chloroacetic anhydride. The solution was stored for 17 h at 22° C. The solution was worked up as before and hydrolysed as usual with 27 ml of 95% ethanol and 5.4 ml of 1 N HCl. After work-up as before there was obtained a gum which was triturated with SKELLYSOLVE B to provide a hydroscopic solid of m.p. 58°-60° C. IR(KBr): 2960, 1755, 1715, 1320, 1295, 1165, 1085, 955 $cm^{-1}$.

Anal. Calc'd for $C_{21}H_{27}ClO_7$: C, 59.08; H, 6.38. Found: C, 60.48; H, 6.66.

Preparation 15

Following the general procedure of Preparation 5 with the bromoacetyl bromide used therein replaced by an equimolar weight of the appropriate acylating agent, the following compounds were prepared:

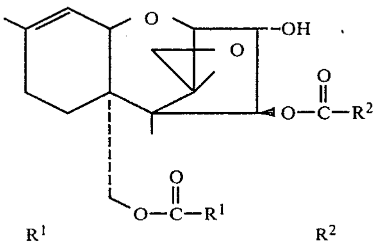

| $R^1$ | $R^2$ |
|---|---|
| $-CH_2CH_3$ | $-CH_2CH_3$ |
| $-CH_2CH_2CH_3$ | $-CH_2CH_2CH_3$ |
| $-CH_2CH_2CH_2CH_3$ | $-CH_2CH_2CH_2CH_3$ |
| 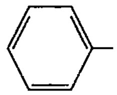 | 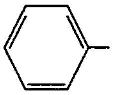 |

Preparation 16

If the general procedure of Preparations 6-7 is repeated with the chloroacetic anhydride used therein replaced by an equimolar amount of the appropriate acylating agent, the following esters may be obtained Product

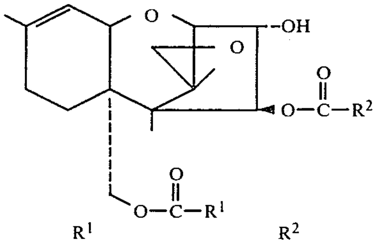

| Acylating Agent | $R^1$ | $R^2$ |
|---|---|---|
| trifluoroacetic anhydride | $-CF_3$ | $-CF_3$ |
| isobutyl chloride | $-CH(CH_3)_2$ | $-CH(CH_3)_2$ |
| valeryl chloride | $-(CH_2)_3CH_3$ | $-(CH_2)_3CH_3$ |
| m-toluoyl chloride | 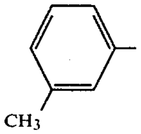 | 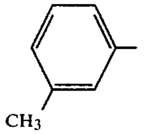 |
| p-anisyl chloride | 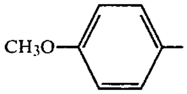 | 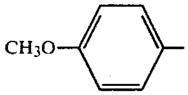 |
| p-chlorobenzoyl chloride | 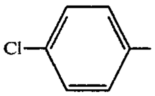 | 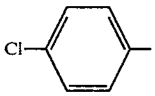 |
| phenylacetyl chloride | 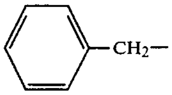 | 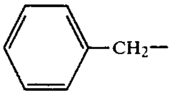 |

Preparation 17

If the general procedure of Preparation 8 is repeated with the chloroacetic anhydride used therein replaced with an equimolar amount of the acylating agents listed in Preparation 16, the following mixed esters may be obtained.

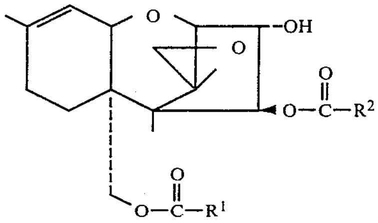

| $R^1$ | $R^2$ |
|---|---|
| $-CH_3$ | $-CF_3$ |
| $-CH_3$ | $-CH(CH_3)_2$ |
| $-CH_3$ | $-(CH_2)_3CH_3$ |
| $-CH_3$ | 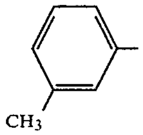 |
| $-CH_3$ | 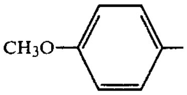 |
| $-CH_3$ | 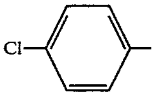 |
| $-CH_3$ | 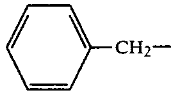 |

Preparation 18

Esters of the type

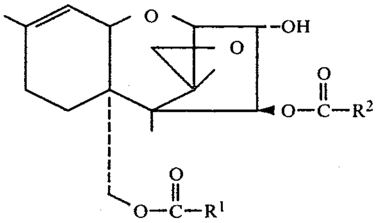

where $R^1 \neq R^2$ may be prepared by a procedure similar to that used for Preparation 14. By using less than two equivalents of an acylating agent listed in Preparation 16, a mixture of monoacylated products of the formulae

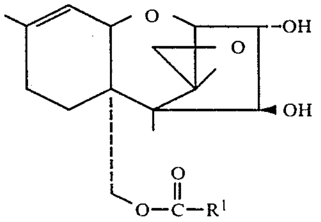

and

-continued

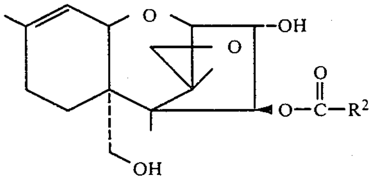

are produced. These products may be separated chromatographically and then treated with a second acylating agent selected from the list provided in Preparation 16 (the second reagent being different than the first) to give products such as shown below.

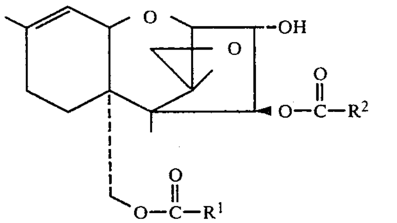

| $R^1$ | $R^2$ |
|---|---|
| $-CF_3$ | 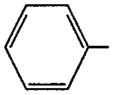 |
| $-CF_3$ | $-CH(CH_3)_2$ |
| 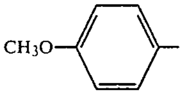 | $-(CH_2)_3CH_3$ |
| 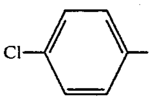 | 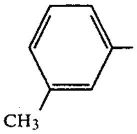 |
| $-CH(CH_3)_2$ | 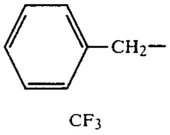 |
| 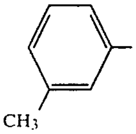 | |

Preparation 19

Following the general procedures illustrated above, the following esters may be prepared.

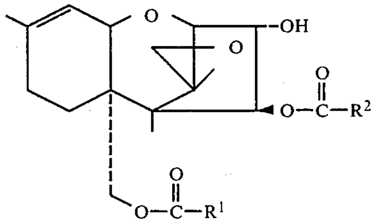

| $R^1$ | $R^2$ |
|---|---|
| $-CH_3$ | $-C(CH_3)=CH_2$ |
| $-C(CH_3)=CH_2$ | $-C(CH_3)=CH_2$ |
| $-C(CH_3)=CH_2$ | $-CH_2Cl$ |
| $-CH=CHCH_3$ | $-CH=CHCH_3$ |
| $-CH_2Cl$ | $-C(CH_3)=CH_2$ |
| $-CH_2CH_2CHClCH_3$ | $-CH_2CH_2CHClCH_3$ |
| $-CH_2CHClCH_3$ | $-CH_2CHClCH_3$ |
| $-CH_2CH(CH_2Cl)CH_3$ | $-CH_2CH(CH_2Cl)CH_3$ |
| $-CCl_3$ | $-CCl_3$ |
| $-CF_3$ | 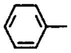 |
| $-CH_3$ | 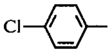 |
| $(CH_3)_2CH-$ | $-CH_2Cl$ |
| 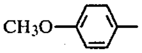 | $-CH_2CH_2CH_3$ |
| 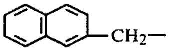 | 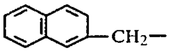 |
| 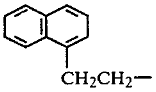 | 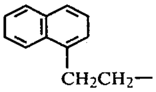 |
| 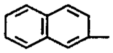 | 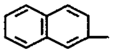 |
| 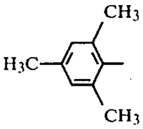 | 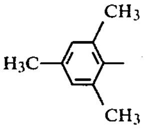 |
| 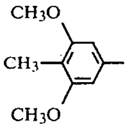 | 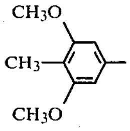 |
| $-CH=CH_2$ | $-CH=CH_2$ |
| $-C(CH_2Br)=CH_2$ | $-C(CH_2Br)=CH_2$ |
| $-C\equiv CCH_3$ | $-C\equiv CCH_3$ |
| $-C\equiv CH$ | $-C\equiv CH$ |
| 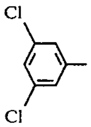 | 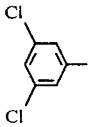 |

-continued

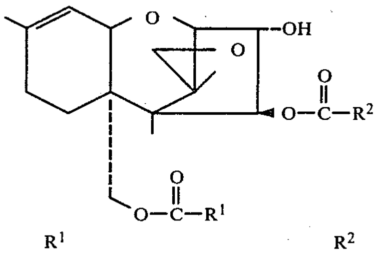

| $R^1$ | $R^2$ |
| --- | --- |
| 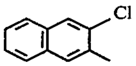 | 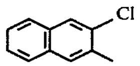 |
| 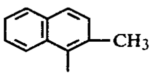 | 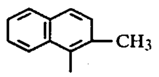 |
| 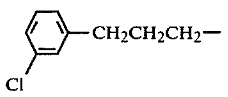 | 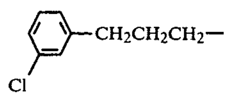 |
| 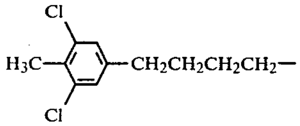 | $-CH_2Cl$ |

EXAMPLE 1

4β,15-Diacetoxy-3α,8β-dihydroxy-12,13-epoxytrichothec-9-ene

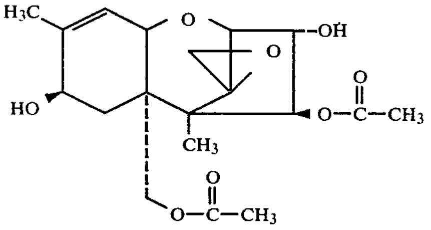

A mixture of 4β,15-diacetoxy-3α-hydroxy-12,13-epoxytrichothec-9-ene (366 mg, 1.0 mmol) of selenium dioxide (122 mg, 1.1 mmol) in 25 ml of dioxane containing 1 ml of water was heated to reflux for 24 h. The resulting solution was filtered through CELITE (diatomaceous earth) and the residue was washed with a small amount of $CH_2Cl_2$. The combined filtrate was diluted with 25 ml of $CH_2Cl_2$ and washed with brine. Drying over $Na_2SO_4$ and removal of the solvent gave 800 mg of an oil. Chromatography on silica gel (elution with 2% methanol-$CH_2Cl_2$) followed by crystallization from $CH_2Cl_2$ and diethyl ether gave 148 mg (39%) of title product as slightly pink crystals. Recrystallization from $CH_2Cl_2$-diethyl ether gave an analytical sample: m.p. 114°-116°; IR (KBr): 3435, 2965, 2943, 2905, 1730, 1715 (sh), 1365, 1248, 1080, 1061, 1035, 958 $cm^{-1}$.

Anal. Calc'd for $C_{19}H_{26}O_8$: C, 59.67; H, 6.85. Found: C, 59.23; H, 6.81.

EXAMPLE 2

15-Acetoxy-4β-chloroacetoxy-3α-hydroxy-12,13-epoxytrichothec-9-en-8-one

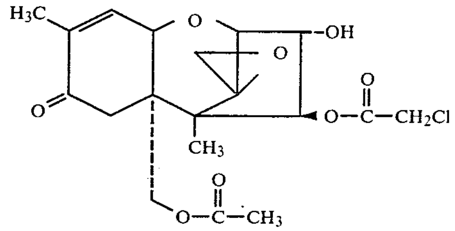

A mixture of 15-acetoxy-4β-chloroacetoxy-3α-hydroxy-12,13-epoxytrichothec-9-ene (0.71 mmol), pyridinium chlorochromate (2.23 mg, 1.03 mmol), and anhydrous sodium acetate (29 mg, 0.35 mmol) in 15 ml of $CH_2Cl_2$ is stirred at room temperature for 2.5 h. After filtration through CELITE, the solvent is removed under reduced pressure to give an oil. Chromatography on silica gel (elution with 0.75% methanol-$CH_2Cl_2$) gives the title product.

EXAMPLE 3

4β,15-Diacetoxy-12,13-epoxytrichothec-9-en-3,8-dione

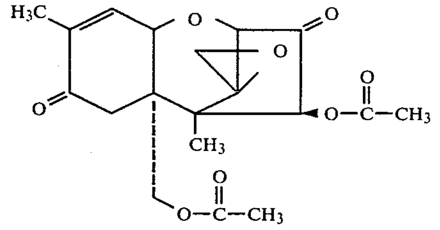

To a solution of 78 mg (1.0 mmol) of dimethyl sulfoxide in 2 ml of $CH_2Cl_2$ was added at −78° C. a 10% $CH_2Cl_2$ solution of trifluoroacetic anhydride (0.6 mmol). After 10 min of stirring at −78° C. a solution of 4β,15-diacetoxy-3α,8β-dihydroxy-12,13-epoxytrichothec-9-ene (76 mg, 0.2 mmol) in $CH_2Cl_2$ (2 ml) was added dropwise. Stirring was continued at −78° C. for 30 min and then triethylamine (101 mg, 1 mmol) was added. After an additional 10 min of stirring at −78° C., the reaction mixture was warmed to room temperature. It was diluted with $CH_2Cl_2$ (25 ml) was washed with brine. Drying over $Na_2SO_4$ and removal of the solvent gave 58 mg (76%) of crystalline solid. Recrystallization from $CH_2Cl_2$ and diethyl ether gave an analytical sample of title product; m.p. 198°-199° C.; IR (KBr): 2990, 2950, 2933, 1780, 1742, 1676, 1392, 1370, 1231, 1220, 1065, 1035 $cm^{-1}$.

Anal. Calc'd for $C_{19}H_{22}O_8$: C, 60.31; H, 5.86. Found: C, 60.19; H, 5.78.

EXAMPLE 4

15-Acetoxy-4β-chloroacetoxy-3α,8β-dihydroxy-12,13-epoxytrichothec-9-ene

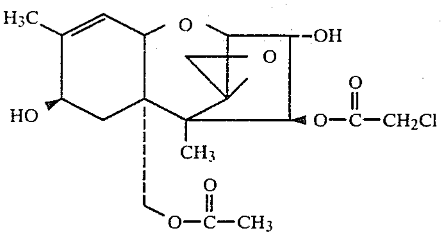

A mixture of 15-acetoxy-4β-chloroacetoxy-3α-hydroxy-12,13-epoxytrichothec-9-ene (653 mg, 1.59 mmol) and selenium dioxide (183 mg, 1.65 mmol) in 25 ml of dioxane containing 1 ml of water was heated to reflux for 12 h. The resulting mixture was filtered through CELITE and the filtrate was evaporated. The residue was dissolved in $CH_2Cl_2$ and washed with brine. Drying over $Na_2SO_4$ and removal of the solvent gave 778 mg of a yellow oil. Chromatography on silica gel (elution with 2% methanol-$CH_2Cl_2$), followed by crystallization from diethyl ether gave 275 mg (42%) of slightly yellow crystals. m.p. 199.5°-200.5° C.; IR (KBr): 3505, 2980, 2950, 1755 (sh), 1740, 1730, 1255, 1238, 1165, 1055 $cm^{-1}$.

Anal. Calc'd for $C_{19}H_{25}ClO_8$: C, 54.74; H, 6.04. Found: C, 54.30; H, 5.84.

EXAMPLE 5

15-Acetoxy-4β-chloroacetoxy-12,13-epoxytrichothec-9-en-3,8-dione

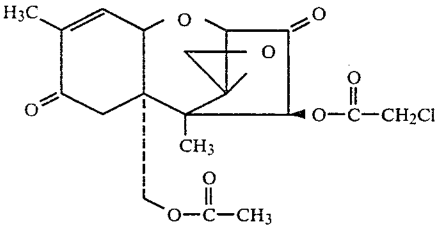

To a solution of dimethyl sulfoxide (0.192 ml, 2.71 mmol) in 3 ml of $CH_2Cl_2$ was added at −78° C. neat trifluoroacetic anhydride (0.217 ml, 1.63 mmol). After 10 min at −78° C., a $CH_2Cl_2$ (5 ml) solution of 15-acetoxy-4β-chloroacetoxy-3α,8β-dihydroxy-12,13-epoxytrichothec-9-ene (245 mg, 0.588 mmol) was added dropwise. The mixture was stirred at −78° for 45 min, followed by a dropwise addition of triethylamine (0.381 ml, 2.71 mmol). The reaction mixture was kept at −78° C. for 10 min and then allowed to warm to room temperature. The resulting solution was diluted with $CH_2Cl_2$ (15 ml) and washed with brine. Drying over $Na_2SO_4$ and removal of the solvent gave 303 mg of oil. Crystallization from diethyl ether yielded 160 mg (66%) of yellow crystals; m.p. 169.5°-171° C. IR (KBr): 3000, 2962, 1772, 1747, 1678, 1232, 1219, 1156, 1052 $cm^{-1}$.

Anal. Calc'd for $C_{19}H_{21}ClO_8$: C, 55.28; H, 5.12. Found: C, 54.31; H, 5.06.

EXAMPLE 6

If the general procedure of Examples 1 and 4 are repeated with the 4β,15-diacetoxy-3α-hydroxy-12,13-epoxytrichothec-9-ene or 15-acetoxy-4β-chloroacetoxy-3α-hydroxy-12,13-epoxytrichothec-9-ene used therein replaced by an equimolar amount of a 3α-hydroxy ester listed below, there is produced the corresponding 3,8-dihydroxy ester product.

Ester Starting Material

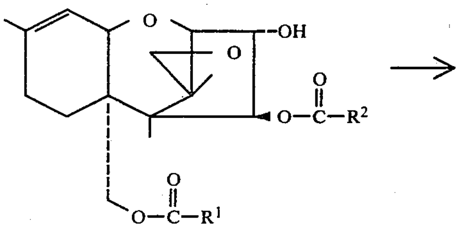

End Product

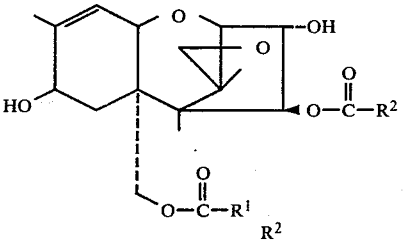

| $R^1$ | $R^2$ |
|---|---|
| $-CH_3$ | $-C(CH_3)=CH_2$ |
| $-C(CH_3)=CH_2$ | $-C(CH_3)=CH_3$ |
| $-C(CH_3)=CH_2$ | $-CH_2Cl$ |
| $-CH=CH(CH_3)$ | $-CH=CH(CH_3)$ |
| $-CH_2Br$ | $-CH_2Br$ |
| $-CH_2Cl$ | $-CH_2Cl$ |
| $-CH_2Cl$ | $-C(CH_3)=CH_2$ |
| $-CH_2CH_3$ | $-CH_2CH_3$ |
| $-CH_2CH_2CH_3$ | $-CH_2CH_2CH_3$ |
| $-CH_2CH_2CH_2CH_3$ | $-CH_2CH_2CH_2CH_3$ |
| $-CH_2CH_2CHClCH_3$ | $-CH_2CH_2CHClCH_3$ |
| $-CH_2CHClCH_3$ | $-CH_2CHClCH_3$ |
| $-CH_2CH(CH_2Cl)CH_3$ | $-CH_2CH(CH_2Cl)CH_3$ |
| $-CCl_3$ | $-CCl_3$ |
| $-CF_3$ | $-CF_3$ |
| 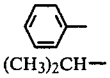 | 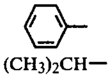 |
| $(CH_3)_2CH-$ | $(CH_3)_2CH-$ |
| 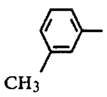 | 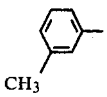 |
| 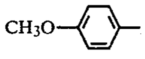 | 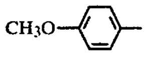 |
| 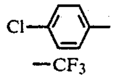 | 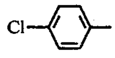 |
| $-CF_3$ | 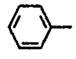 |
| $-CH_3$ | 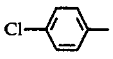 |

-continued

Ester Starting Material

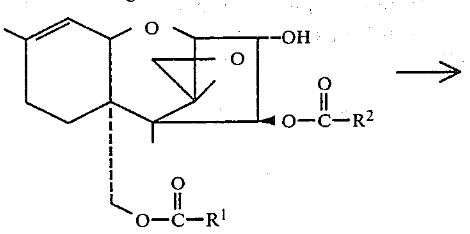

End Product

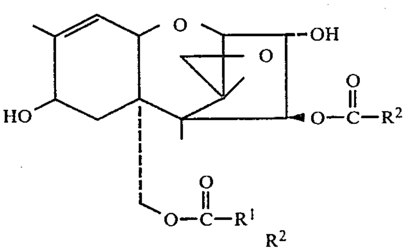

| $R^1$ | $R^2$ |
|---|---|
| $(CH_3)_2CH-$ | $-CH_2Cl$ |
| 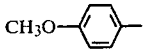 | $-CH_2CH_2CH_3$ |
| 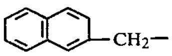 | 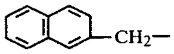 |
| 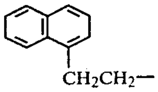 | 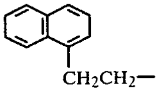 |
| 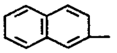 | 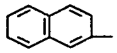 |
| 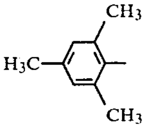 | 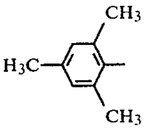 |
| 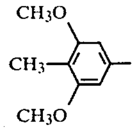 | 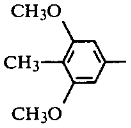 |
| 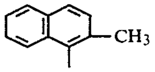 | 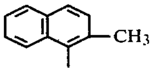 |
| 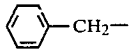 | 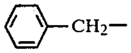 |
| 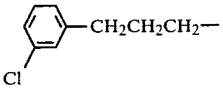 | 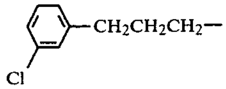 |
| 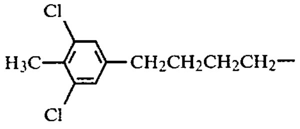 | $-CH_2Cl$ |

EXAMPLE 7

If the general procedure of Example 2 is repeated with the 15-acetoxy-4β-chloroacetoxy-3α-hydroxy-12,13-epoxytrichothec-9-ene used therein replaced by an equimolar amount of a 3,8-dihydroxy ester listed below, there is produced the corresponding 3α-hydroxy-8-keto product.

Starting Material

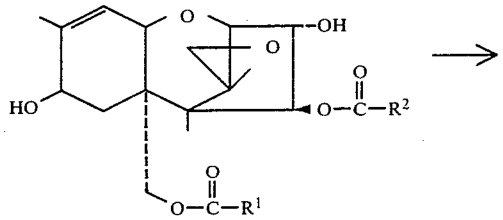

End Product

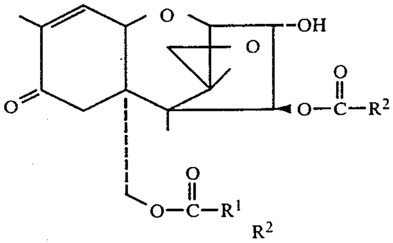

| $R^1$ | $R^2$ |
|---|---|
| $-CH_3$ | $-\underset{CH_3}{\underset{\vert}{C}}=CH_2$ |
| $-\underset{CH_3}{\underset{\vert}{C}}=CH_2$ | $-\underset{CH_3}{\underset{\vert}{C}}=CH_3$ |
| $-\underset{CH_3}{\underset{\vert}{C}}=CH_2$ | $-CH_2Cl$ |
| $-CH=\underset{CH_3}{\underset{\vert}{CH}}$ | $-CH=\underset{CH_3}{\underset{\vert}{CH}}$ |
| $-CH_2Br$ | $-CH_2Br$ |
| $-CH_2Cl$ | $-CH_2Cl$ |
| $-CH_2Cl$ | $-\underset{CH_3}{\underset{\vert}{C}}=CH_2$ |
| $-CH_2CH_3$ | $-CH_2CH_3$ |
| $-CH_2CH_2CH_3$ | $-CH_2CH_2CH_3$ |
| $-CH_2CH_2CH_2CH_3$ | $-CH_2CH_2CH_2CH_3$ |
| $-CH_2CH_2CHClCH_3$ | $-CH_2CH_2CHClCH_3$ |
| $-CH_2CHClCH_3$ | $-CH_2CHClCH_3$ |
| $-CH_2\underset{CH_2Cl}{\underset{\vert}{C}H}CH_3$ | $-CH_2\underset{CH_2Cl}{\underset{\vert}{C}H}CH_3$ |
| $-CCl_3$ | $-CCl_3$ |
| $-CF_3$ | $-CF_3$ |
| 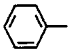 | 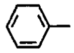 |
| $(CH_3)_2CH-$ | $(CH_3)_2CH-$ |
| 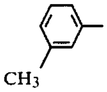 | 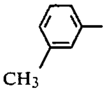 |
| 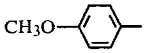 | 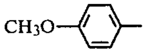 |
| 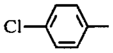 | 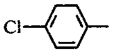 |
| $-CF_3$ | 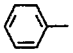 |
| $-CH_3$ | 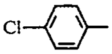 |
| $(CH_3)_2CH-$ | $-CH_2Cl$ |
| 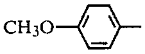 | $-CH_2CH_2CH_3$ |
| 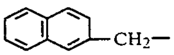 | 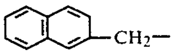 |

-continued

Starting Material

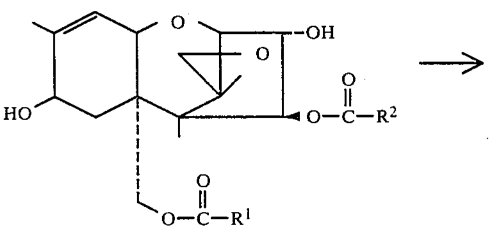

End Product

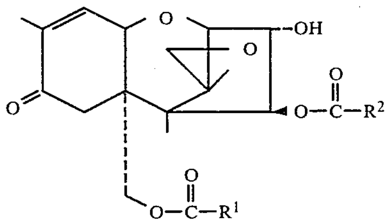

| R1 | R2 |
|---|---|
| 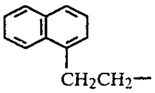 | 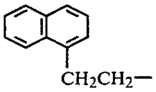 |
| 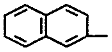 | 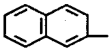 |
| 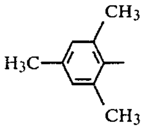 | 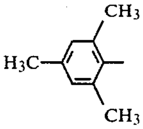 |
| 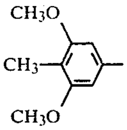 | 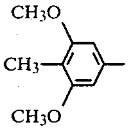 |
| 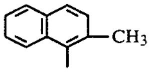 | 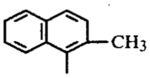 |
| 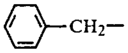 | 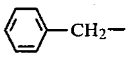 |
| 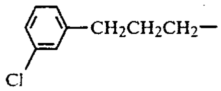 | 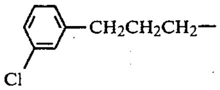 |
| 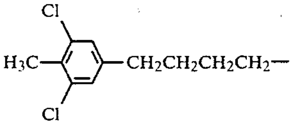 | $-CH_2Cl$ |

EXAMPLE 8

If the general procedures of Examples 3 and 5 are repeated with the 4β,15-diacetoxy-3α,8β-dihydroxy-12,13-epoxytrichothec-9-ene or 15-acetoxy-4β-chloroacetoxy-3α,8β-dihydroxy-12,13-epoxytrichothec-9-ene used therein replaced by an equimolar amount of a 3,8-dihydroxy ester listed below, there is produced the corresponding 3,8-diketo product.

Starting Material

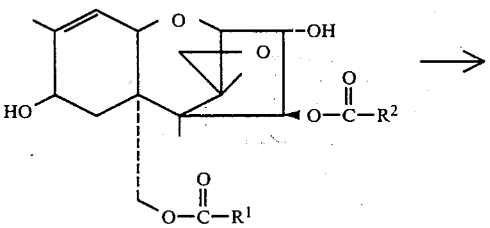

End Product

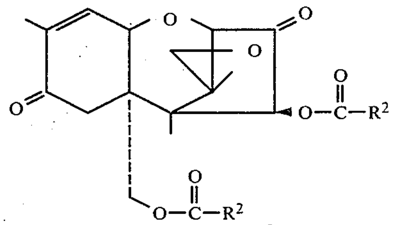

| R1 | R2 |
|---|---|
| $-CH_3$ | $-C=CH_2$<br>$CH_3$ |
| $-C=CH_2$<br>$CH_3$ | $-C=CH_3$<br>$CH_3$ |
| $-C=CH_2$<br>$CH_3$ | $-CH_2Cl$ |
| $-CH=CH$<br>$CH_3$ | $-CH=CH$<br>$CH_3$ |
| $-CH_2Br$ | $-CH_2Br$ |
| $-CH_2Cl$ | $-CH_2Cl$ |
| $-CH_2Cl$ | $-C=CH_2$<br>$CH_3$ |
| $-CH_2CH_3$ | $-CH_2CH_3$ |
| $-CH_2CH_2CH_3$ | $-CH_2CH_2CH_3$ |
| $-CH_2CH_2CH_2CH_3$ | $-CH_2CH_2CH_2CH_3$ |
| $-CH_2CH_2CHClCH_3$ | $-CH_2CH_2CHClCH_3$ |
| $-CH_2CHClCH_3$ | $-CH_2CHClCH_3$ |
| $-CH_2CHCH_3$<br>$CH_2Cl$ | $-CH_2CHCH_3$<br>$CH_2Cl$ |
| $-CCl_3$ | $-CCl_3$ |
| $-CF_3$ | $-CF_3$ |
| 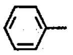 | 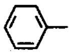 |
| $(CH_3)_2CH-$ | $(CH_3)_2CH-$ |
| 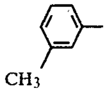 | 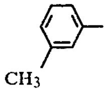 |
| 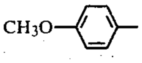 | 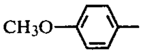 |
| 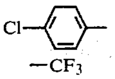 | 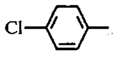 |
| $-CF_3$ | 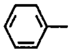 |
| $-CH_3$ | 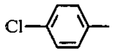 |
| $(CH_3)_2CH-$ | $-CH_2Cl$ |
| 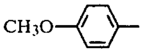 | $-CH_2CH_2CH_3$ |
| 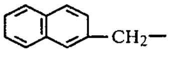 | 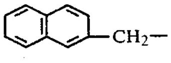 |

-continued

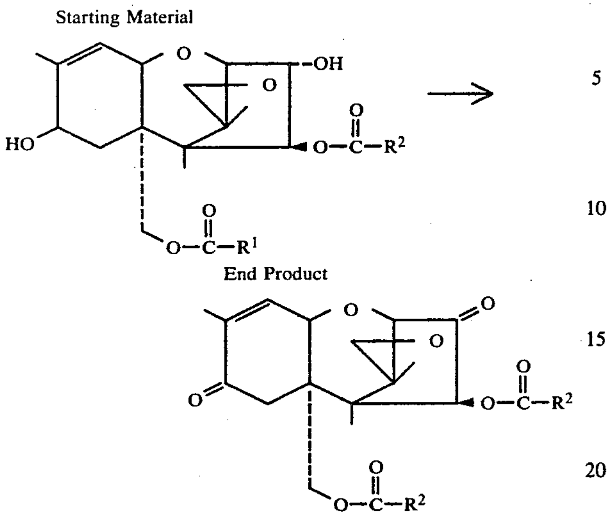

| $R^1$ | $R^2$ |
|---|---|
| 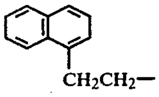 | 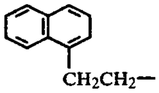 |
| 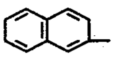 | 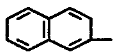 |
| 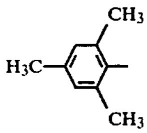 | 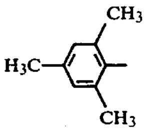 |
| 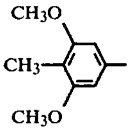 | 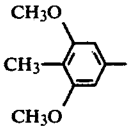 |
| 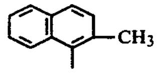 | 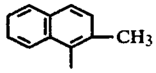 |
| 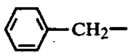 | 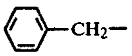 |
| 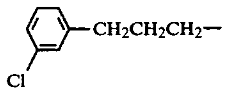 | 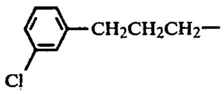 |
| 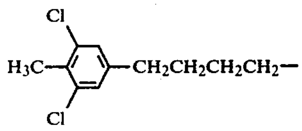 | $-CH_2Cl$ |

This invention is capable of industrial application.

We claim:

1. A compound of the formula

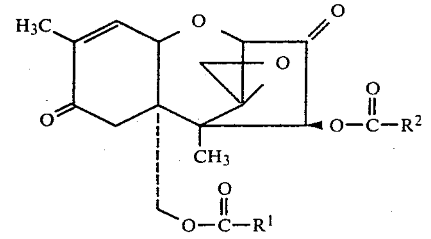

wherein $R^1$ and $R^2$ are each independently (lower)alkyl; halo(lower)alkyl; alkenyl of the formula $-CR^3{=}CR^4R^5$ in which $R^3$ is hydrogen, (lower)alkyl or 1'-halo(lower)alkyl and $R^4$ and $R^5$ are each independently hydrogen or (lower)alkyl; alkynyl of the formula $-C{\equiv}CR^6$ in which $R^6$ is hydrogen or (lower)alkyl; or a radical of the formula $$Ar-(CH_2)_m-$$

in which m is 0 or an integer from one to four and Ar is

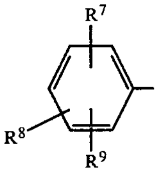

or

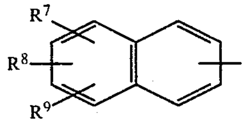

wherein $R^7$, $R^8$ and $R^9$ are each independently hydrogen, halogen, (lower)alkyl or (lower)alkoxy.

2. A compound as claimed in claim 1 wherein $R^1$ and $R^2$ are each independently (lower)alkyl, halo(lower)alkyl or $-CR^3{=}CR^4R^5$ in which $R^3$, $R^4$ and $R^5$ are each independently hydrogen or (lower)alkyl.

3. A compound as claimed in claim 1 wherein $R^1$ and $R^2$ are each independently (lower)alkyl, $-CH_2Cl$ or

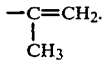

4. The compound of claim 1 wherein $R^1$ and $R^2$ are each methyl.

5. The compound of claim 1 wherein $R^1$ is $-CH_3$ and $R^2$ is $-CH_2Cl$.

6. The compound of claim 1 wherein $R^1$ is $-CH_3$ and $R^2$ is

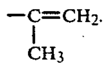

7. The compound of claim 1 wherein $R^1$ and $R^2$ are each

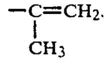

* * * * *